US010067329B2

(12) United States Patent
Kubo (10) Patent No.: US 10,067,329 B2
(45) Date of Patent: Sep. 4, 2018

(54) MICROSCOPE APPARATUS AND SPECIMEN OBSERVATION METHOD (71) Applicant: OLYMPUS CORPORATION, Hachioji-shi, Tokyo (JP)

(72) Inventor: Hirokazu Kubo, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/494,658

(22) Filed: Apr. 24, 2017

(65) Prior Publication Data
US 2017/0336611 A1 Nov. 23, 2017

(30) Foreign Application Priority Data

May 23, 2016 (JP) ................. 2016-102040

(51) Int. Cl.
G02B 21/02 (2006.01)
G01N 21/64 (2006.01)
G02B 21/16 (2006.01)
G02B 21/06 (2006.01)
G02B 21/04 (2006.01)

(52) U.S. Cl.
CPC ......... G02B 21/02 (2013.01); G01N 21/6458 (2013.01); G02B 21/04 (2013.01); G02B 21/06 (2013.01); G02B 21/16 (2013.01); G01N 2021/6478 (2013.01); G01N 2201/06113 (2013.01)

(58) Field of Classification Search
CPC ........ G02B 21/02; G02B 21/04; G02B 21/16; G02B 21/06; G01N 21/6458; G01N 2021/6478; G01N 2201/06113

USPC ........................................... 250/458.1, 459.1
See application file for complete search history.

(56) References Cited

U.S. PATENT DOCUMENTS 5,717,519 A * 2/1998 Sugiyama .......... G02B 21/0024
359/234
2005/0001157 A1* 1/2005 Ishida ................ G02B 21/0044
250/234

(Continued)

FOREIGN PATENT DOCUMENTS

JP 3015912 B2 3/2000
JP 5633706 B2 12/2014

Primary Examiner — David Porta
Assistant Examiner — Gisselle Gutierrez
(74) Attorney, Agent, or Firm — Holtz, Holtz & Volek PC (57) ABSTRACT A microscope apparatus provided with: a disk unit obtained by integrally forming a pinhole array disk in which pinholes are arranged and a microlens array disk in which microlenses are arranged; a dichroic mirror focusing illumination light that has been transmitted through the microlenses of the disk unit, on the corresponding pinholes and splitting off fluorescence from a specimen that has passed through the pinholes in the reverse direction from the illumination light; an objective lens radiating the illumination light that has passed through the pinholes onto the specimen and focusing the fluorescence from the specimen on the pinholes; an illumination-light-axis adjustment mechanism adjusting the position and the angle of the optical axis of the illumination light; an installation-angle adjustment mechanism adjusting the installation angle of the disk unit; and a unit insertion/removal mechanism removably supporting the disk unit onto the optical axis of the illumination light.

7 Claims, 10 Drawing Sheets

(56) References Cited

U.S. PATENT DOCUMENTS

| | | | |
|---|---|---|---|
| 2005/0002091 A1* | 1/2005 | Amano | G02B 21/0032 359/368 |
| 2008/0037114 A1* | 2/2008 | Sheblee | G02B 21/0044 359/385 |
| 2008/0278801 A1* | 11/2008 | Koike | G02B 21/16 359/385 |
| 2013/0148184 A1* | 6/2013 | Azuma | G02B 21/08 359/223.1 |
| 2015/0042779 A1* | 2/2015 | Hayashi | G02B 21/0076 348/79 |
| 2016/0103309 A1* | 4/2016 | Suzuki | G02B 27/145 359/388 |

\* cited by examiner

MICROSCOPE APPARATUS AND SPECIMEN OBSERVATION METHOD

CROSS-REFERENCE TO RELATED APPLICATIONS

This application is based on Japanese Patent Application No. 2016-102040, the contents of which are incorporated herein by reference.

TECHNICAL FIELD

The present invention relates to a microscope apparatus and a specimen observation method.

BACKGROUND ART

There are conventionally-known disk-scanning-type confocal microscopes that are provided with a disk unit in which a microlens array and a pinhole array having the same pattern are integrally assembled (for example, see PTL 1 and PTL 2).

In the confocal microscope described in PTL 1, a shift of the illumination light axis due to a dichroic mirror is corrected by inclining the angle of the optical axis of illumination light with respect to the incident axis of the microlens array or by inclining the installation angle of the disk unit with respect to the incident axis of an objective lens. In the confocal microscope described in PTL 2, it is possible to switch among a plurality of disk units that have different pinhole diameters, and the incident angle of illumination light with respect to the disk unit is adjusted in conjunction with the switching of the disk units, thereby avoiding a reduction in the amount of light passing through the pinholes and improving the signal-to-noise ratio of the image.

CITATION LIST

Patent Literature

{PTL 1} Publication of Japanese Patent No. 3015912
{PTL 2} Publication of Japanese Patent No. 5633706

SUMMARY OF INVENTION

Technical Problem

The present invention provides a microscope apparatus and a specimen observation method capable of acquiring a high-definition image in which image shift is suppressed, while ensuring sufficient illumination intensity on the specimen surface.

Solution to Problem

According to one aspect, the present invention provides a microscope apparatus including: a disk unit that is obtained by integrally forming a first disk in which a plurality of minute openings are arranged in an arrayed manner around a central shaft and a second disk that is disposed with a gap with respect to the first disk in the direction of the central shaft and in which a plurality of microlenses are arranged in an arrayed manner around the central shaft in the same pattern as the plurality of minute openings; a rotary drive portion that rotates the disk unit about the central shaft; a beam splitter that focuses illumination light transmitted through the microlenses of the disk unit on the minute openings corresponding to the microlenses and that splits off, from the light path of the illumination light, observation light from a specimen, which has passed through the minute openings in the reverse direction from the illumination light; an objective lens that radiates the illumination light that has passed through the minute openings onto the specimen and that collects the observation light from the specimen and guides the observation light to the minute openings; an illumination-light-axis adjustment portion that can adjust the position and the angle of the optical axis of illumination light incident on the beam splitter; an installation-angle adjustment portion that can adjust an installation angle of the disk unit; and a unit support portion that supports the disk unit in a manner allowing the disk unit to be removably inserted onto the optical axis of the illumination light.

The above-described aspect may further include a position adjustment portion that can adjust the position of the objective lens in a direction intersecting the optical axis of the illumination light.

In the above-described aspect, the illumination-light-axis adjustment portion may be provided with: an optical-axis adjustment memory that can store adjustment amounts for the position and the angle of the optical axis of the illumination light in a state in which the disk unit is removed from the optical axis of the illumination light and in a state in which the disk unit is inserted onto the optical axis of the illumination light; and an optical-axis electric drive unit that adjusts the position and the angle of the optical axis of the illumination light on the basis of the adjustment amounts stored in the optical-axis adjustment memory.

The above-described aspect may further include a plurality of the disk units that have different minute opening diameters from each other, wherein the unit support portion supports the disk units in a switchable manner allowing the disk units to be removably inserted onto the optical axis of the illumination light; and the installation-angle adjustment portion is provided with: a disk adjustment memory that can store an adjustment amount for the installation angle of the disk unit in the state in which any one of the plurality of the disk unit is inserted onto the optical axis of the illumination light; and a disk electric drive unit that adjusts the installation angle of the disk unit on the basis of the adjustment amount stored in the disk adjustment memory.

The above-described aspect may further include a plurality of the disk units that have different minute opening diameters from each other; and a plurality of the installation-angle adjustment portions that can adjust the installation angles of the disk units individually, wherein the unit support portion supports the disk units in a switchable manner allowing the disk units to be removably inserted onto the optical axis of the illumination light.

According to another aspect, the present invention provides a specimen observation method using a microscope apparatus, the method including the steps of: radiating illumination light onto a specimen; detecting observation light that returns, from the specimen irradiated with the illumination light, via the light path of the illumination light in the reverse direction; adjusting the position and the angle of the optical axis of the illumination light in a state in which a disk unit is removed from the optical axis of the illumination light, the disk unit being obtained by integrally forming a first disk in which a plurality of minute openings are arranged in an arrayed manner around a central shaft and a second disk in which a plurality of microlenses are arranged in an arrayed manner around the central shaft in the same pattern as the plurality of minute openings; adjusting, thereafter, the installation angle of the disk unit in the state in which the disk unit is inserted onto the optical axis of the illumination light; and adjusting, thereafter, the angle of the optical axis of the illumination light and the installation angle of the disk unit in the state in which the disk unit is still inserted onto the optical axis of the illumination light.

According to still another aspect, the present invention provides a specimen observation method using a microscope apparatus, the method including the steps of: radiating illumination light onto a specimen; detecting observation light that returns, from the specimen irradiated with the illumination light, via the light path of the illumination light in the reverse direction; adjusting the position and the angle of the optical axis of the illumination light in the state in which a disk unit is removed from the optical axis of the illumination light, the disk unit being obtained by integrally forming a first disk in which a plurality of minute openings are arranged in an arrayed manner around a central shaft and a second disk in which a plurality of microlenses are arranged in an arrayed manner around the central shaft in the same pattern as the plurality of minute openings; adjusting, thereafter, the installation angle of the disk unit in the state in which the disk unit is inserted onto the optical axis of the illumination light; and adjusting, thereafter, the position of the objective lens in a direction intersecting the optical axis of the illumination light in the state in which the disk unit is still inserted onto the optical axis of the illumination light.

DESCRIPTION OF EMBODIMENTS

First Embodiment

A microscope apparatus and a specimen observation method according to a first embodiment of the present invention will be described below with reference to the drawings.

Figure 1:
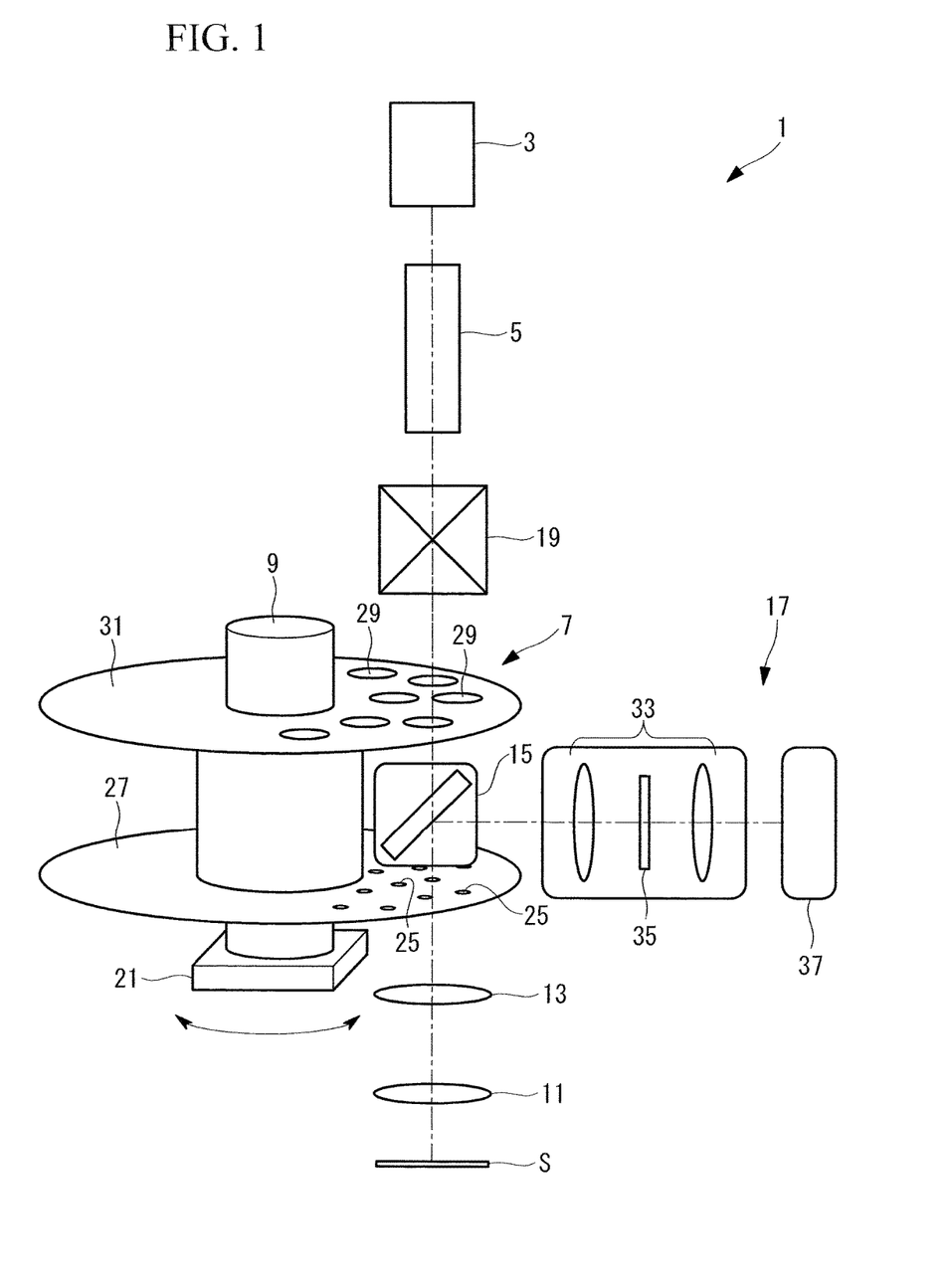
FIG. 1 is a view showing, in outline, the configuration of a microscope apparatus according to a first embodiment of the present invention.

A microscope apparatus 1 of this embodiment is provided with: a light source 3, such as a laser light source, that emits illumination light; an illumination optical system 5 that shapes the illumination light emitted from the light source 3 into a desired beam; a disk unit 7 that has a plurality of pinholes (minute openings) 25 and microlenses 29; a rotary drive portion (not shown), such as a motor, that rotates the disk unit 7 about a rotary shaft 9; an objective lens 11 that radiates the illumination light that has been transmitted through the disk unit 7 onto a specimen S and that collects fluorescence (observation light) from the specimen S; an image forming lens 13 that focuses the fluorescence collected by the objective lens 11, thus forming an image; a plate dichroic mirror (beam splitter) 15 that splits off the fluorescence focused by the image forming lens 13; and a fluorescence detection system 17 that detects the fluorescence split off by the dichroic mirror 15.

Figure 2:
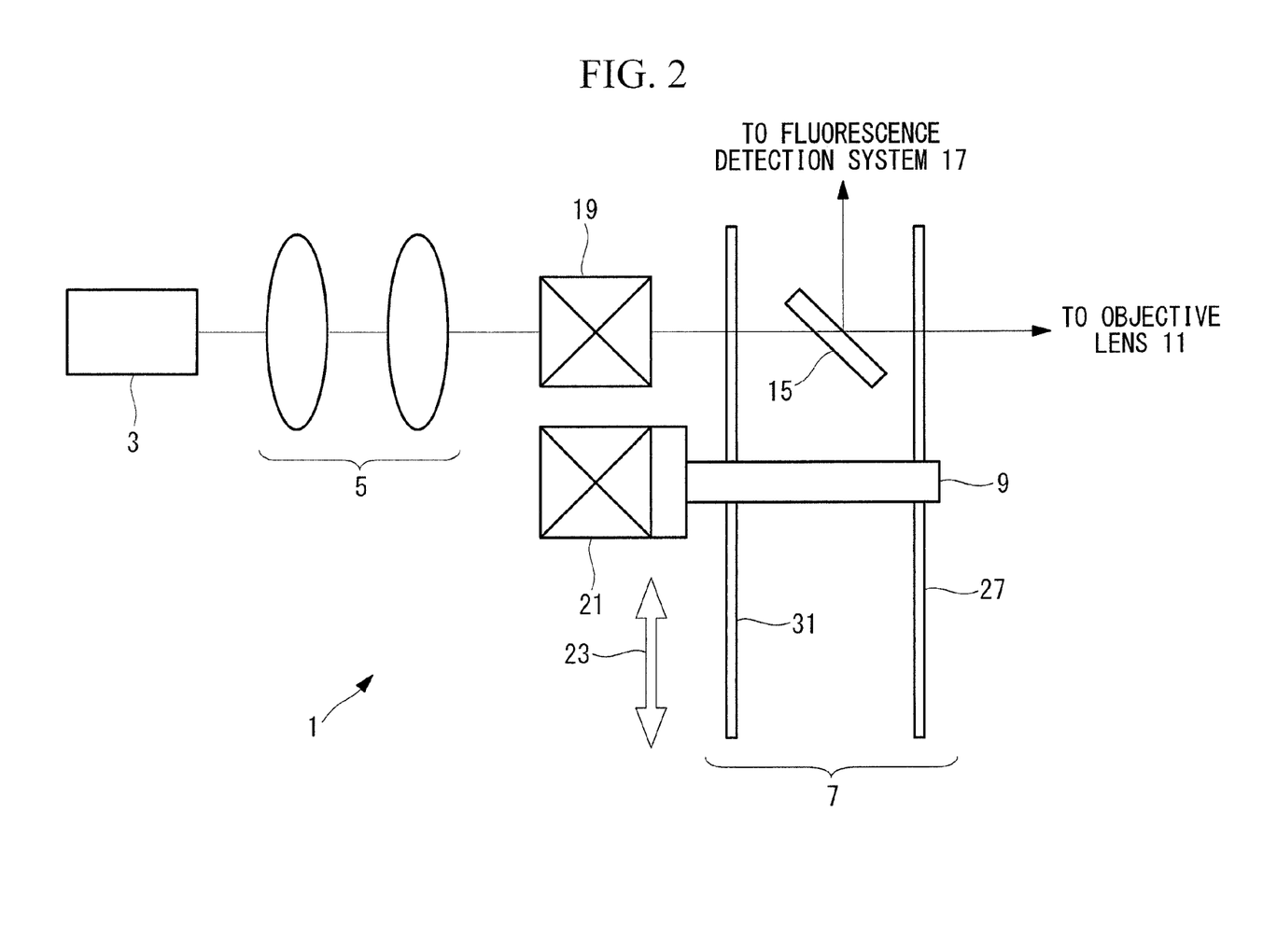
FIG. 2 is a view showing the vicinity of an illumination-light-axis adjustment mechanism, an installation-angle adjustment mechanism, and a unit insertion/removal mechanism that are shown in FIG. 1.

As shown in FIG. 2, the microscope apparatus 1 is provided with: an illumination-light-axis adjustment mechanism (illumination-light-axis adjustment portion) 19 that can adjust the position and the angle of the axis of illumination light incident on the dichroic mirror 15; an installation-angle adjustment mechanism (installation-angle adjustment portion) 21 that can adjust the installation angle of the disk unit 7; and a unit insertion/removal mechanism (unit support portion) 23 that supports the disk unit 7 in a manner allowing it to be removably inserted onto the optical axis of illumination light.

As shown in FIG. 1, the disk unit 7 is provided with: a pinhole array disk (first disk) 27 in which the plurality of pinholes 25 are arranged in an arrayed manner around the rotary shaft 9; and a microlens array disk (second disk) 31 in which the plurality of microlenses 29 are arranged in an arrayed manner around the rotary shaft 9.

In the disk unit 7, the microlens array disk 31 is disposed on the light source 3 side, the pinhole array disk 27 is disposed on the specimen S side, and the microlens array disk 31 and the pinhole array disk 27 are coaxially provided with a gap therebetween in the direction of the rotary shaft 9. The microlens array disk 31 and the pinhole array disk 27 are integrally rotated about the common rotary shaft 9 by the rotary drive portion. The direction along the rotary shaft 9 is referred to as the Z-direction, and directions intersecting the rotary shaft 9 are referred to as the X-direction and the Y-direction.

In the disk unit 7, the pinholes 25 of the pinhole array disk 27 and the microlenses 29 of the microlens array disk 31 are formed in the same pattern, and the pinholes 25 and the microlenses 29 are arranged in association with each other. Therefore, illumination light incident on the microlenses 29 is focused on the pinholes 25 corresponding to those microlenses 29. Of the fluorescence focused by the image forming lens 13, the pinholes 25 allow only the fluorescence that is produced at the focal position of the objective lens 11 in the specimen S to pass therethrough.

The dichroic mirror 15 is disposed on the optical axis of illumination light, between the microlens array disk 31 and the pinhole array disk 27. The dichroic mirror 15 transmits illumination light that is focused, by the microlenses 29, on the corresponding pinholes 25 and reflects fluorescence from the specimen S that has passed through the pinholes 25, toward the fluorescence detection system 17.

The fluorescence detection system 17 is provided with: a relay optical system 33 that relays the fluorescence from the dichroic mirror 15; an absorption filter 35 that absorbs illumination light returning from the specimen S together with the fluorescence, thus allowing only the fluorescence to pass therethrough; and an image acquisition device 37, such as a camera, that detects the fluorescence relayed by the relay optical system 33 to obtain image information.

Figure 3:
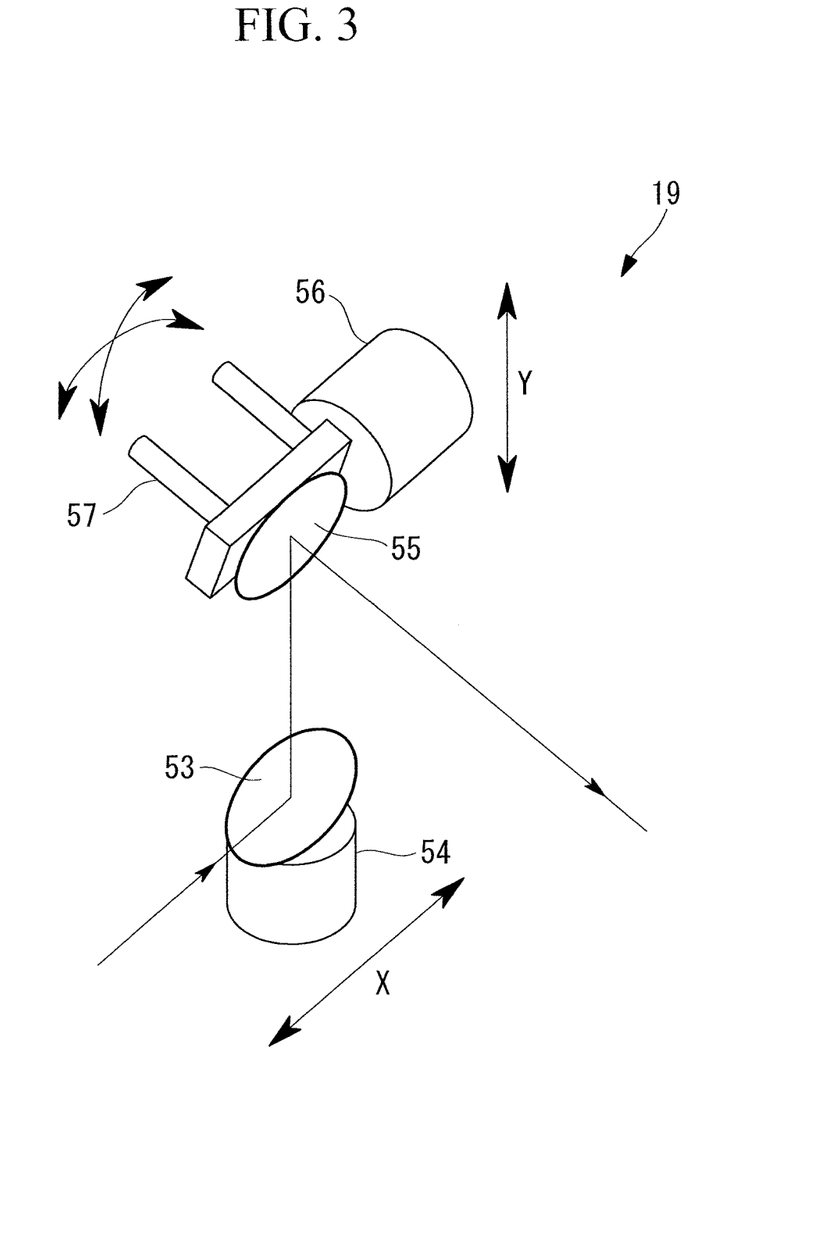
FIG. 3 is a view showing, in outline, the configuration of the illumination-light-axis adjustment mechanism shown in FIG. 2.

As shown in FIG. 3, for example, the illumination-light-axis adjustment mechanism 19 is provided with: a first reflecting mirror 53 that reflects illumination light from the illumination optical system 5; a uniaxial X stage 54 that can adjust the position of the first reflecting mirror 53 in the X-direction; a second reflecting mirror 55 that reflects the illumination light reflected by the first reflecting mirror 53, toward the microlens array disk 31; and a uniaxial Y stage 56 that can adjust the position of the second reflecting mirror 55 in the Y-direction.

The first reflecting mirror 53 is fixed on the uniaxial X stage 54 at an inclination of 45 degrees. The uniaxial X stage 54 can move the first reflecting mirror 53 in the X-direction.

The second reflecting mirror 55 is disposed on the uniaxial Y stage 56 at an inclination of 45 degrees. The uniaxial Y stage 56 can move the second reflecting mirror 55 in the Y-direction. The second reflecting mirror 55 is provided with an angle adjustment knob 57 that can adjust the inclination of the second reflecting mirror 55.

The illumination-light-axis adjustment mechanism 19 can shift the optical axis of illumination light incident on the dichroic mirror 15, in the X-direction and in the Y-direction, by moving the first reflecting mirror 53 in the X-direction by means of the uniaxial X stage 54 and by moving the second reflecting mirror 55 in the Y-direction by means of the uniaxial Y stage 56. The illumination-light-axis adjustment mechanism 19 can incline the optical axis of illumination light in the X-direction and in the Y-direction by inclining the second reflecting mirror 55 by means of the angle adjustment knob 57.

The installation-angle adjustment mechanism 21 can incline the rotary shaft 9 of the disk unit 7 in the X-direction and in the Y-direction.

The unit insertion/removal mechanism 23 can insert the disk unit 7 onto the optical axis of illumination light to dispose the microlenses 29 and the pinholes 25 in the light path of illumination light and can remove the whole disk unit 7 from the optical axis of illumination light.

Figure 4:
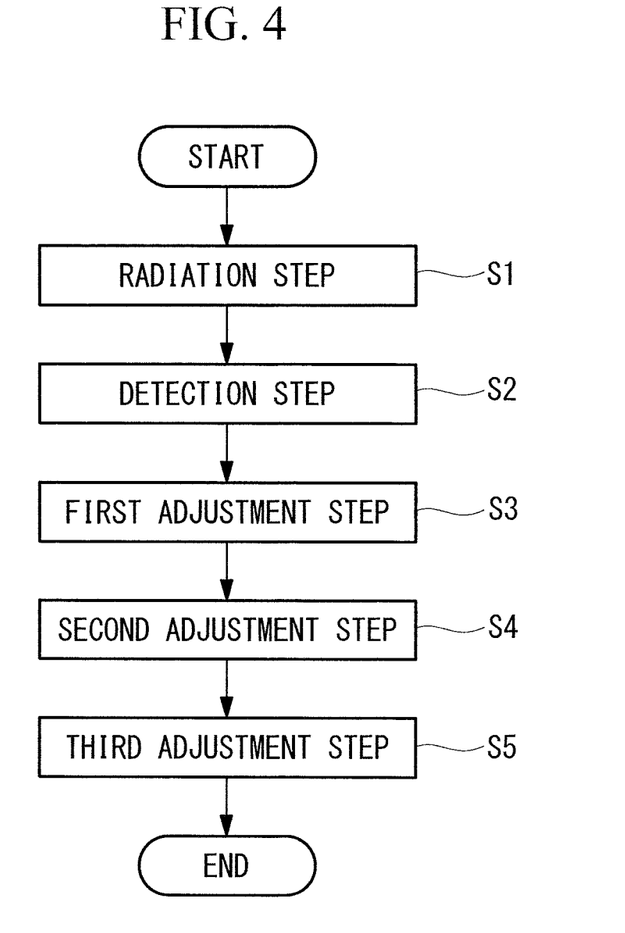
FIG. 4 is a flowchart for explaining a specimen observation method according to the first embodiment of the present invention.

Next, as shown in FIG. 4, a specimen observation method of this embodiment includes: a radiation step S1 of radiating, by means of the objective lens 11, illumination light emitted from the light source 3 onto the specimen S; a detection step S2 of detecting, by means of the fluorescence detection system 17, fluorescence produced in the specimen S irradiated with the illumination light in the radiation step S1; a first adjustment step S3 of adjusting the position and the angle of the optical axis of illumination light with the disk unit 7 removed from the optical axis of illumination light; a second adjustment step S4 of adjusting the installation angle of the disk unit 7 with the disk unit 7 inserted onto the optical axis of illumination light, after the first adjustment step S3; and a third adjustment step S5 of adjusting the angle of the optical axis of illumination light and the installation angle of the disk unit 7 with the disk unit 7 still inserted onto the optical axis of illumination light, after the second adjustment step S4.

The operation of the thus-configured microscope apparatus 1 and the specimen observation method will be described with reference to the flowchart of FIG. 4.

In order to observe the specimen S by using the microscope apparatus 1 and the specimen observation method of this embodiment, first, the disk unit 7 is removed from the optical axis of illumination light by the unit insertion/removal mechanism 23, and illumination light is emitted from the light source 3.

The illumination light emitted from the light source 3 is shaped into a desired beam by the illumination optical system 5, passes through the illumination-light-axis adjustment mechanism 19, is transmitted through the dichroic mirror 15, passes through the image forming lens 13, and is radiated onto the specimen S by the objective lens 11 (the radiation step S1).

Fluorescence produced in the specimen S by radiating the illumination light thereonto is collected by the objective lens 11, returns via the light path of the illumination light, is focused by the image forming lens 13, and is reflected by the dichroic mirror 15 toward the fluorescence detection system 17. The fluorescence reflected by the dichroic mirror 15 is relayed by the relay optical system 33, passes through the absorption filter 35, and is detected by the image acquisition device 37 (the detection step S2). Accordingly, image information of the specimen S based on the detected fluorescence is acquired in the image acquisition device 37.

Here, when the illumination light is transmitted through the dichroic mirror 15, a shift occurs in the optical axis of the illumination light. Thus, a user adjusts, by using the illumination-light-axis adjustment mechanism 19, the position and the angle of the optical axis of the illumination light in the X-direction and in the Y-direction with the disk unit 7 removed from the optical axis of the illumination light, to align the optical axis of the illumination light with the optical axis of the objective lens 11 (the first adjustment step S3). Accordingly, a shift in the illumination light axis due to the dichroic mirror 15 is corrected, the amount of fluorescence detected by the image acquisition device 37 is maximized, and so-called image shift is reduced. Image shift means a shift in the position of an image in a direction intersecting the optical axis when the focus position is shifted in the optical axis direction in an in-focus state.

Next, the user inserts the disk unit 7 onto the optical axis of the illumination light by means of the unit insertion/removal mechanism 23 and rotates the disk unit 7 about the rotary shaft 9 by means of the rotary drive portion. Illumination light emitted from the light source 3 and focused by the illumination optical system 5 passes through the illumination-light-axis adjustment mechanism 19 and is incident on the disk unit 7.

The illumination light incident on the disk unit 7 is focused by the microlenses 29 that are arranged in the light path of the illumination light, is transmitted through the dichroic mirror 15, passes through the pinholes 25 that are similarly arranged in the optical axis of the illumination light, passes through the image forming lens 13, and is radiated onto the specimen S by the objective lens 11. The microlenses 29 and the pinholes 25 through which the illumination light passes are changed in succession due to the rotation of the disk unit 7, thereby moving the spot position of the illumination light according to the pattern of the microlenses 29 and the pinholes 25 and scanning the illumination light on the specimen S.

Fluorescence that is produced in the specimen S by radiating the illumination light thereonto, that is collected by the objective lens 11, and that returns via the light path of the illumination light is focused by the image forming lens 13, passes through the pinholes 25, is reflected by the dichroic mirror 15, passes through the relay optical system 33 and the absorption filter 35, and is detected by the image acquisition device 37.

Here, the user adjusts the installation angle of the disk unit 7 in accordance with the inclination of the illumination light axis by means of the installation-angle adjustment mechanism 21, with the disk unit 7 inserted onto the optical axis of illumination light, to maximize the amount of transmitted illumination light in the disk unit 7 (the second adjustment step S4). At this time, the microlenses 29 are inclined, thereby causing image shift.

Thus, with the disk unit 7 still inserted onto the optical axis of illumination light, the user repeatedly fine-adjusts the angle of the optical axis of illumination light by means of the illumination-light-axis adjustment mechanism 19 and repeatedly fine-adjusts the installation angle of the disk unit 7 by means of the installation-angle adjustment mechanism 21 (the third adjustment step S5). Accordingly, the image shift caused by inclining the disk unit 7 is reduced while preventing the amount of fluorescence detected by the image acquisition device 37 from being reduced, as much as possible.

As a result, it is possible to suppress image shift while ensuring as much transmitted illumination light in the disk unit 7 and as much detected fluorescence as possible. Therefore, the image acquisition device 37 acquires a bright image with high S/N on the basis of the fluorescence from the specimen S on which the illumination light has been scanned, thus making it possible to observe the specimen S.

As described above, according to the microscope apparatus 1 and the specimen observation method of this embodiment, the disk unit 7 is temporarily removed from the optical axis of illumination light, and the incident optical axis of illumination light on the dichroic mirror 15 is made appropriate; then, the disk unit 7 is inserted onto the optical axis of illumination light, and the incident optical axis of illumination light on the disk unit 7 is also made appropriate, thereby making it possible to suppress image shift and to acquire a high-definition image while ensuring sufficient illumination intensity on the specimen surface.

This embodiment can be modified as follows.

Figure 5:
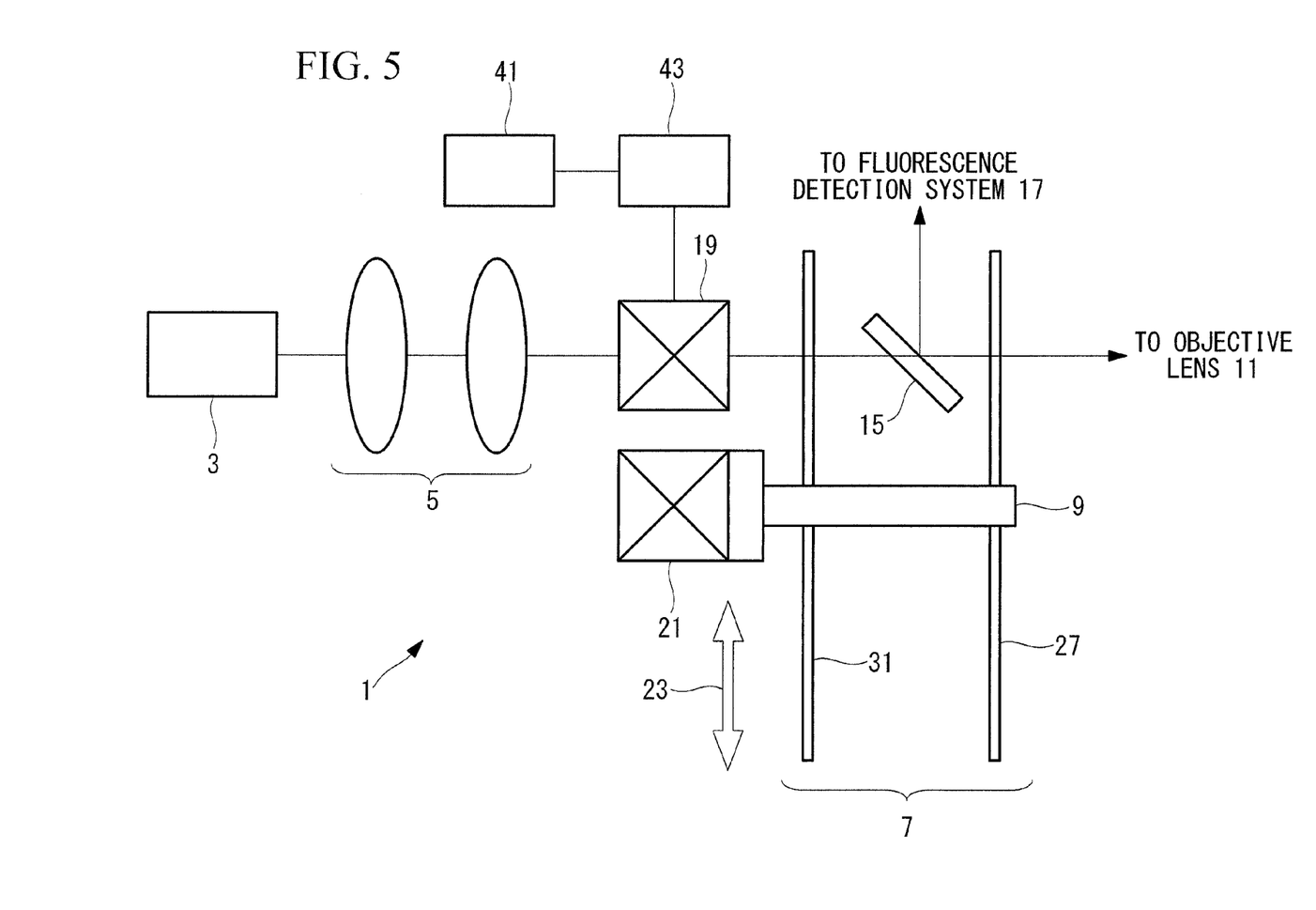
FIG. 5 is a view showing, in outline, the configuration of a microscope apparatus according to a first modification of the first embodiment of the present invention.

As a first modification, for example, as shown in FIG. 5, the illumination-light-axis adjustment mechanism 19 may be provided with: an optical-axis adjustment memory 41 that can store adjustment amounts for the position and the angle of the optical axis of illumination light in the X-direction and in the Y-direction in the state in which the disk unit 7 is removed from the optical axis of illumination light and in the state in which the disk unit 7 is inserted onto the optical axis of illumination light; and an electric actuator (optical-axis electric drive unit) 43 that adjusts the position and the angle of the optical axis of illumination light on the basis of the adjustment amounts stored in the optical-axis adjustment memory 41.

In this case, the user may preliminarily adjust the position and the angle of the optical axis of illumination light through the first adjustment step S3 to the third adjustment step S5 and may store the adjustment amounts in the optical-axis adjustment memory 41 in advance.

When the unit insertion/removal mechanism 23 inserts the disk unit 7 onto the optical axis of the illumination light, the unit insertion/removal mechanism 23 may send an insertion signal to the electric actuator 43, and, when the unit insertion/removal mechanism 23 removes the disk unit 7 from the optical axis of the illumination light, the unit insertion/removal mechanism 23 may send a removal signal to the electric actuator 43. Then, every time the insertion signal and the removal signal are sent from the unit insertion/removal mechanism 23, the electric actuator 43 may adjust the position and the angle of the optical axis of illumination light in the X-direction and in the Y-direction on the basis of the adjustment amounts stored in the optical-axis adjustment memory 41.

By doing so, in either of the state in which the disk unit 7 is inserted onto the optical axis of illumination light and the state in which the disk unit 7 is removed from the optical axis thereof, the electric actuator 43 can automatically set appropriate illumination light with ease and accuracy. In the state in which the disk unit 7 is removed from the optical axis of illumination light, an appropriate illumination light axis can be obtained through bright-field fluorescence observation.

Figure 6:
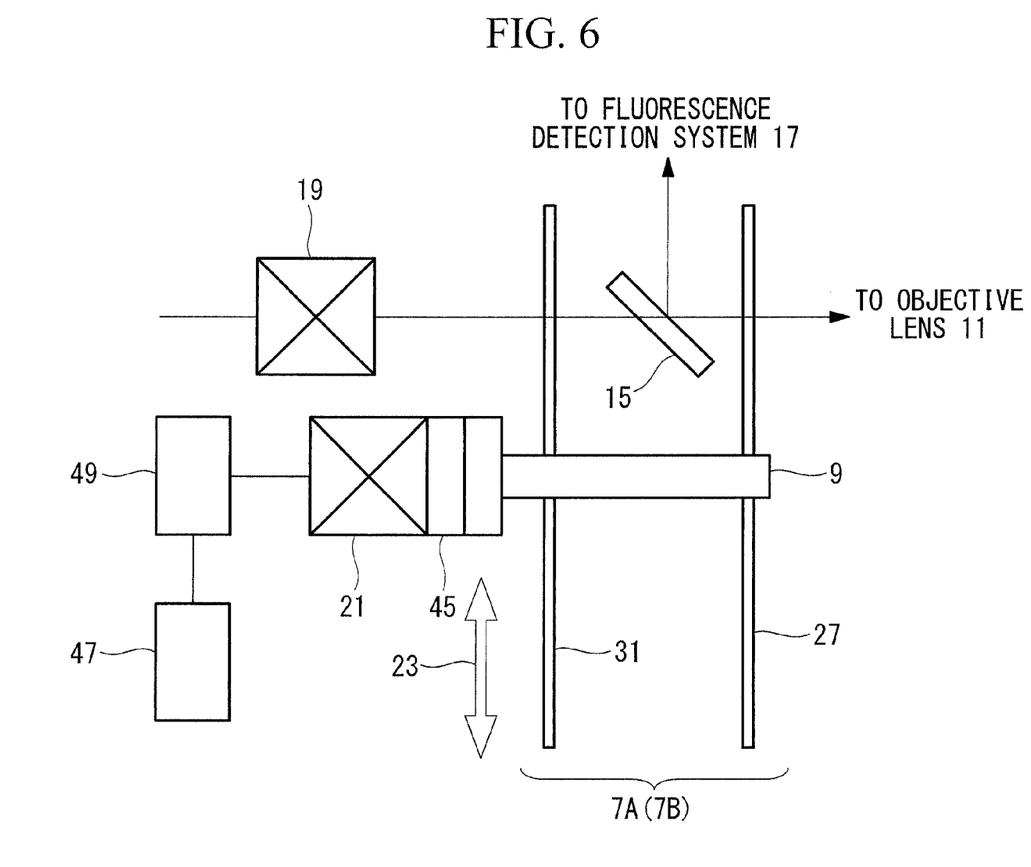
FIG. 6 is a view showing, in outline, the configuration of a microscope apparatus according to a second modification of the first embodiment of the present invention.
Figure 7:
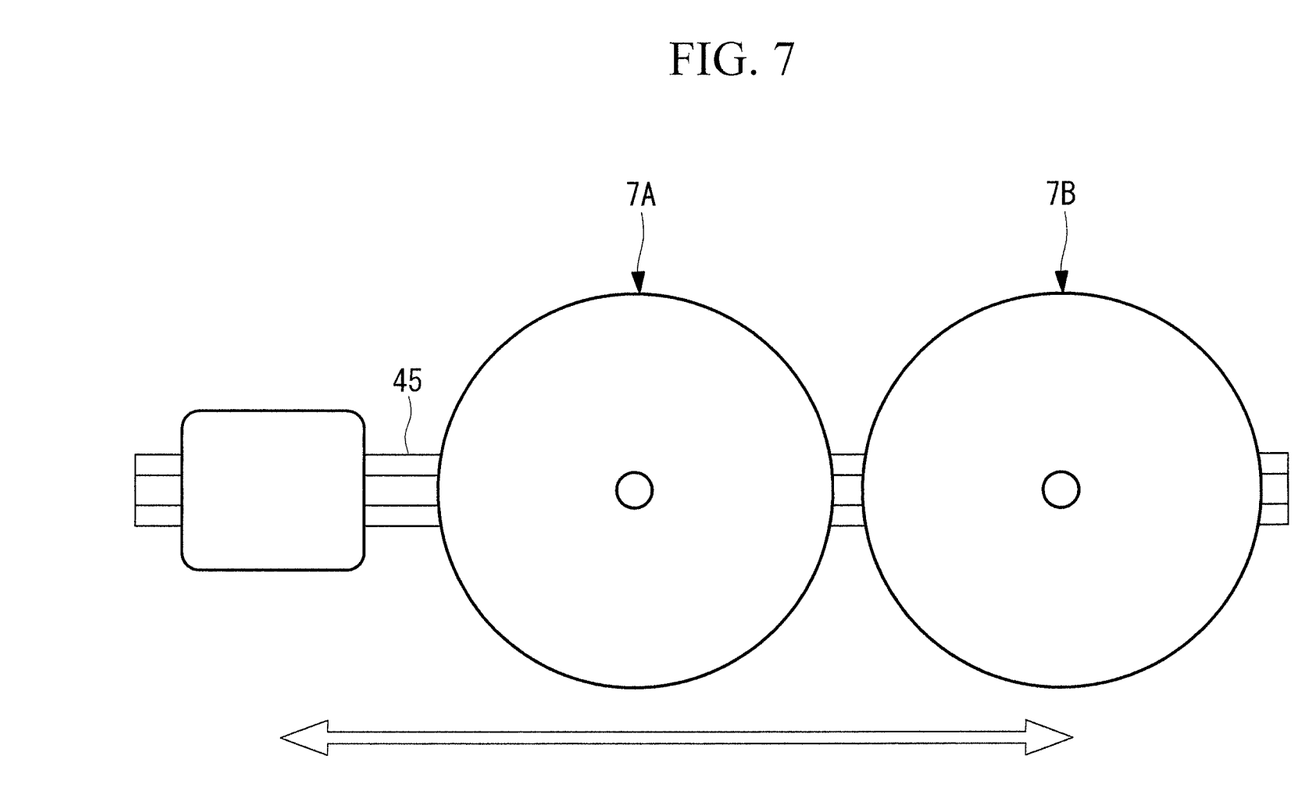
FIG. 7 is a view showing the vicinity of disk units and an installation-angle adjustment mechanism shown in FIG. 6.

As a second modification, for example, as shown in FIGS. 6 and 7, two disk units 7A and 7B that have different opening diameters of the multiple pinholes 25 from each other may be provided, and the unit insertion/removal mechanism 23 may be provided with a unit switching mechanism 45 that switches between the disk units 7A and 7B to be selectively inserted onto or removed from the optical axis of illumination light.

The installation-angle adjustment mechanism 21 may be provided with: a disk adjustment memory 47 that can store an adjustment amount for the installation angle of the disk unit 7A or 7B with the disk unit 7A or 7B inserted onto the optical axis of illumination light; and an electric actuator (disk electric drive unit) 49 that adjusts the installation angle of the disk unit 7A or 7B on the basis of the adjustment amount stored in the disk adjustment memory 47.

In this case, the user may preliminarily adjust the installation angle of the disk unit 7 through the first adjustment step S3 to the third adjustment step S5 and may store the adjustment amount in the disk adjustment memory 47 in advance.

When the disk unit 7A or 7B is selectively inserted onto the optical axis of illumination light by the unit insertion/removal mechanism 23 and the unit switching mechanism 45, the unit insertion/removal mechanism 23 may send, to the electric actuator 49, an insertion signal of the disk unit 7A or 7B disposed on the optical axis of illumination light, and, when the disk units 7A and 7B are both removed from the optical axis of illumination light, the unit insertion/removal mechanism 23 may send a removal signal to the electric actuator 49. Then, every time the insertion signal and the removal signal are sent from the unit insertion/removal mechanism 23, the electric actuator 49 may adjust the installation angle of the disk unit 7A or 7B disposed on the optical axis of illumination light on the basis of the adjustment amount stored in the disk adjustment memory 47.

By doing so, the electric actuator 49 can automatically set, for each of the disk units 7A and 7B, an installation angle for ensuring as much transmitted light in the disk unit 7A or 7B as possible. Therefore, the disk unit 7A or 7B whose pinholes 25 have minute opening diameters corresponding to the numerical aperture (NA) of the objective lens 11 is selectively used, thereby making it possible to optimize the optical conditions, such as resolution, brightness, etc. of an image. In this modification, although a description has been given of an example case in which the two disk units 7A and 7B are provided, it is also possible to provide three or more disk units that respectively have a plurality of pinholes 25 with different opening diameters, in a manner allowing switching among the disk units.

Figure 8A:
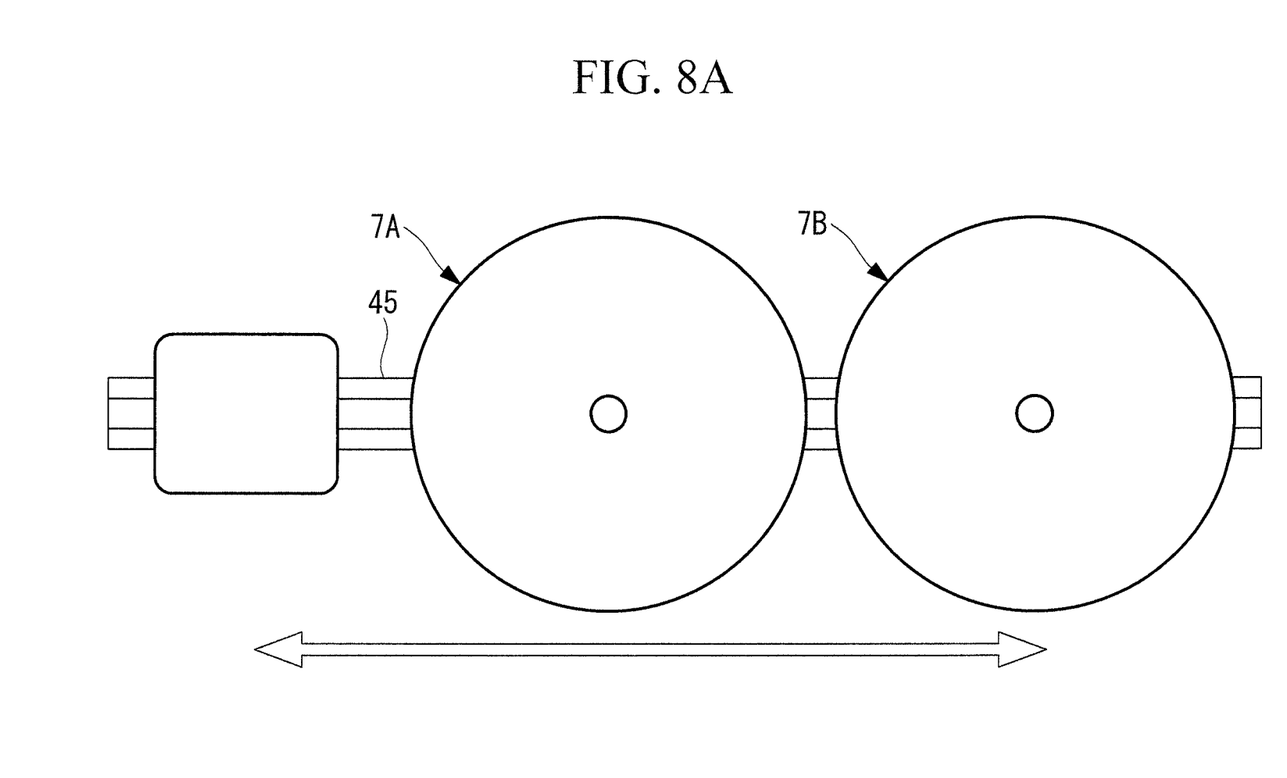
FIG. 8A is a view showing, in outline, the configuration of another microscope apparatus according to the second modification of the first embodiment of the present invention.
Figure 8B:
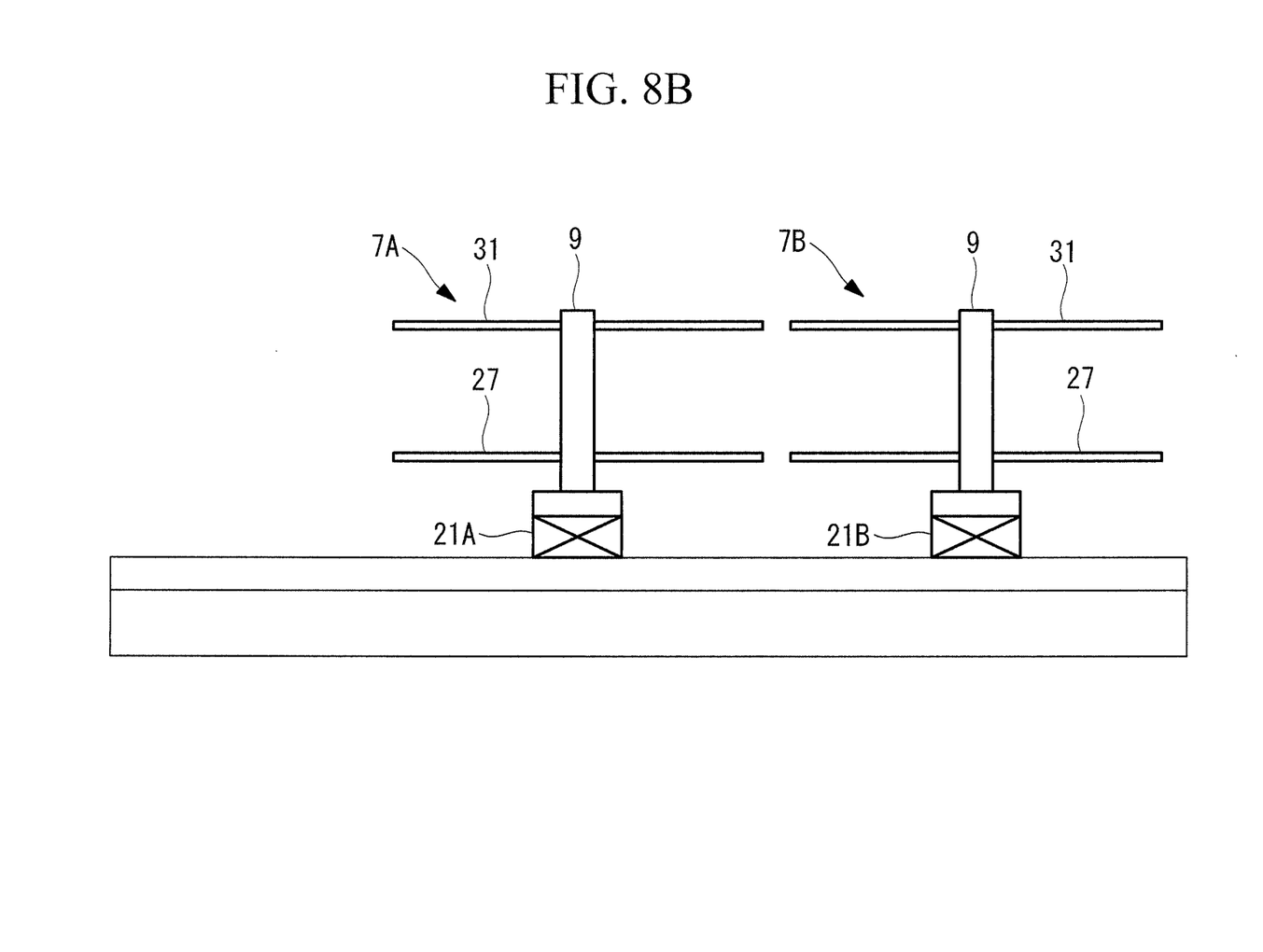
FIG. 8B is a view showing the vicinity of disk units and installation-angle adjustment mechanisms shown in FIG. 8A.

In this modification, for example, as shown in FIGS. 8A and 8B, it is also possible to provide installation-angle adjustment mechanisms 21A and 21B for the disk units 7A and 7B, respectively. Each of the installation-angle adjustment mechanisms 21A and 21B need not be provided with the electric actuator 49; the installation angles of the disk units 7A and 7B may be individually adjusted manually.

By doing so, when the disk unit is switched to one of the disk units 7A and 7B that has the pinholes 25 with the minute opening diameters corresponding to the numerical aperture (NA) of the objective lens 11, the user precisely adjusts the installation angle for the disk unit 7A or 7B by means of the corresponding installation-angle adjustment mechanism 21A or 21B, thereby making it possible to optimize the optical conditions, such as resolution, brightness, etc. of an image. Since the electric actuator 49 is not adopted, it is possible to provide an inexpensive structure.

Second Embodiment

Next, a microscope apparatus and a specimen observation method according to a second embodiment of the present invention will be described.

Figure 9:
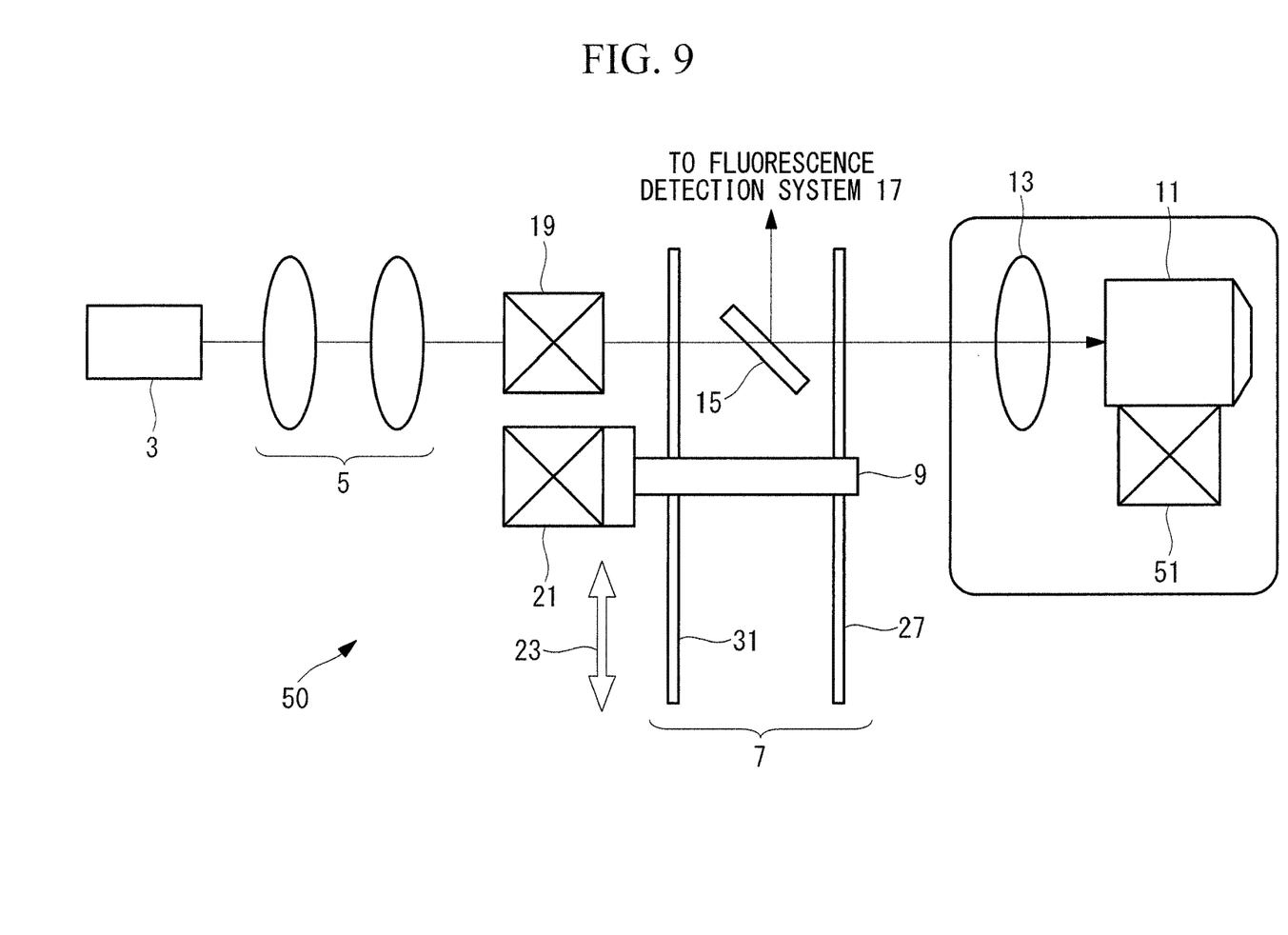
FIG. 9 is a view showing, in outline, the configuration of a microscope apparatus according to a second embodiment of the present invention.

As shown in FIG. 9, a microscope apparatus 50 of this embodiment differs from that of the first embodiment in that a position adjustment mechanism (position adjustment portion) 51 that can adjust the position of the objective lens 11 in the X-direction and the Y-direction, which intersect the optical axis of illumination light, is provided.

Identical reference signs are assigned to portions having configurations common to those in the microscope apparatus 1 and the specimen observation method of the first embodiment, and a description thereof will be omitted.

In the third adjustment step S5 of the specimen observation method of this embodiment, the position of the objective lens 11 in the X-direction and the Y-direction, which intersect the optical axis of illumination light, is fine-adjusted by the position adjustment mechanism 51, instead of adjusting the angle of the optical axis of illumination light and the installation angle of the disk unit 7 with the disk unit 7 still inserted onto the optical axis of illumination light, after the second adjustment step S4. Steps from the radiation step S1 to the second adjustment step S4 are the same as those in the first embodiment, and thus a description thereof will be omitted.

The operation of the thus-configured microscope apparatus 50 and specimen observation method will be described.

In order to observe the specimen S by using the microscope apparatus 50 and the specimen observation method of this embodiment, after the second adjustment step S4, the user fine-adjusts the position of the objective lens 11 in the X-direction and in the Y-direction by means of the position adjustment mechanism 51 with the disk unit 7 still inserted onto the optical axis of illumination light, to increase the amount of fluorescence to be detected by the image acquisition device 37 (the third adjustment step S5).

Accordingly, in the third adjustment step S5, compared with a case in which the angle of the optical axis of illumination light and the installation angle of the disk unit 7 are respectively adjusted, it is possible to suppress image shift while ensuring as much transmitted illumination light in the disk unit 7 and as much detected fluorescence as possible, with ease and accuracy.

Therefore, according to the microscope apparatus 50 and the specimen observation method of this embodiment, ensuring sufficient illumination intensity on the specimen surface and suppressing image shift are easily achieved, thereby making it possible to acquire a higher definition image.

Although the embodiments of the present invention have been described above in detail with reference to the drawings, specific configurations are not limited to those embodiments, and design changes that do not depart from the scope of the present invention are also encompassed. For example, the present invention is not limited to those applied to the above-described embodiments and modifications; it can also be applied to embodiment that is obtained by appropriately combining the embodiments and the modifications, and is not particularly limited. In the above-described embodiments, although a description has been given of the pinholes 25 as example minute openings, instead of this, for example, the plurality of minute openings may be a plurality of slits that are formed around the rotary shaft 9 in the same pattern as the plurality of microlenses 29.

As a result, the following forms are derived from the above-described embodiments.

According to one form, the present invention provides a microscope apparatus including: a disk unit that is obtained by integrally forming a first disk in which a plurality of minute openings are arranged in an arrayed manner around a central shaft and a second disk that is disposed with a gap with respect to the first disk in the direction of the central shaft and in which a plurality of microlenses are arranged in an arrayed manner around the central shaft in the same pattern as the plurality of minute openings; a rotary drive portion that rotates the disk unit about the central shaft; a beam splitter that focuses illumination light transmitted through the microlenses of the disk unit on the minute openings corresponding to the microlenses and that splits off, from the light path of the illumination light, observation light from a specimen, which has passed through the minute openings in the reverse direction from the illumination light; an objective lens that radiates the illumination light that has passed through the minute openings onto the specimen and that collects the observation light from the specimen and guides the observation light to the minute openings; an illumination-light-axis adjustment portion that can adjust the position and the angle of the optical axis of illumination light incident on the beam splitter; an installation-angle adjustment portion that can adjust an installation angle of the disk unit; and a unit support portion that supports the disk unit in a manner allowing the disk unit to be removably inserted onto the optical axis of the illumination light.

According to the above-described form, illumination light that has been transmitted through the microlenses of the disk unit, which is rotated about the central shaft by the rotary drive portion, and that has been focused via the beam splitter passes through the minute openings corresponding to the microlenses and is sequentially radiated onto the specimen by the objective lens, thereby being scanned on the specimen. Therefore, observation light that returns from the specimen irradiated with the illumination light, that passes through the objective lens and the same minute openings in the reverse direction from the illumination light, and that is split off by the beam splitter is detected, thereby making it possible to obtain image information of the specimen based on the brightness of the observation light.

In this case, the position and the angle of the optical axis of the illumination light are adjusted by means of the illumination-light-axis adjustment portion with the disk unit removed from the optical axis of the illumination light by the unit support portion, to align the optical axis of the illumination light with the optical axis of the objective lens, thereby making it possible to increase the amount of detected observation light and to reduce so-called image shift. Image shift means a shift in the position of an image in a direction intersecting the optical axis when the focus position is shifted in the optical axis direction in an in-focus state.

In this state, the disk unit is inserted onto the optical axis of the illumination light by the unit support portion, and the installation angle of the disk unit is adjusted in accordance with the inclination of the illumination light axis by means of the installation-angle adjustment portion, thereby making the amount of transmitted illumination light in the disk unit appropriate, whereas the microlenses are inclined, thereby causing image shift. Thus, from this state, the angle of the optical axis of the illumination light is further fine-adjusted by means of the illumination-light-axis adjustment portion, and the installation angle of the disk unit is fine-adjusted by means of the installation-angle adjustment portion, thereby making it possible to suppress image shift while ensuring as much transmitted illumination light in the disk unit and as much detected observation light as possible. Accordingly, while ensuring sufficient illumination intensity on the specimen surface, a high-definition image in which image shift is suppressed can be acquired.

The above-described form may further include a position adjustment portion that can adjust the position of the objective lens in a direction intersecting the optical axis of the illumination light.

With this configuration, only the position of the objective lens in a direction intersecting the optical axis of the illumination light is adjusted by means of the position adjustment portion, thereby making it possible to easily align the optical axis of the objective lens with the optical axis of the illumination light.

Therefore, the position and the angle of the optical axis of the illumination light are adjusted with the disk unit removed from the optical axis of the illumination light, the disk unit is then inserted onto the optical axis of the illumination light by the unit support portion, the installation angle of the disk unit is fine-adjusted by means of the installation-angle adjustment portion, and the position of the objective lens in a direction intersecting the optical axis of the illumination light is fine-adjusted by means of the position adjustment portion; thus, compared with a case in which the installation angle of the disk unit and the angle of the optical axis of the illumination light are adjusted, it is possible to suppress image shift while ensuring as much transmitted illumination light in the disk unit and as much detected observation light as possible, with ease and accuracy. Accordingly, ensuring sufficient illumination intensity on the specimen surface and suppressing image shift are easily achieved, thereby making it possible to acquire a higher definition image.

In the above-described form, the illumination-light-axis adjustment portion may be provided with: an optical-axis adjustment memory that can store adjustment amounts for the position and the angle of the optical axis of the illumination light in a state in which the disk unit is removed from the optical axis of the illumination light and in a state in which the disk unit is inserted onto the optical axis of the illumination light; and an optical-axis electric drive unit that adjusts the position and the angle of the optical axis of the illumination light on the basis of the adjustment amounts stored in the optical-axis adjustment memory.

With this configuration, in either of the state in which the disk unit is inserted onto the optical axis of illumination light and the state in which the disk unit is removed from the optical axis thereof, it is possible to automatically set appropriate illumination light with ease and accuracy.

The above-described form may further include a plurality of the disk units that have different minute opening diameters from each other, wherein the unit support portion supports the disk units in a switchable manner allowing the disk units to be removably inserted onto the optical axis of the illumination light; and the installation-angle adjustment portion is provided with: a disk adjustment memory that can store an adjustment amount for the installation angle of the disk unit in the state in which any one of the plurality of the disk unit is inserted onto the optical axis of the illumination light; and a disk electric drive unit that adjusts the installation angle of the disk unit on the basis of the adjustment amount stored in the disk adjustment memory.

With this configuration, the disk electric drive unit can automatically set, for each of the disk units, an installation angle for ensuring as much transmitted light in the disk unit as possible. Therefore, the disk unit that has minute opening diameters corresponding to the numerical aperture (NA) of the objective lens is used, thereby making it possible to optimize the optical conditions, such as resolution, brightness, etc. of an image.

The above-described form may further include: a plurality of the disk units that have different minute opening diameters from each other; and a plurality of the installation-angle adjustment portions that can adjust the installation angles of the disk units individually, wherein the unit support portion supports the disk units in a switchable manner allowing the disk units to be removably inserted onto the optical axis of the illumination light.

With this configuration, when the disk unit is switched to the disk unit that has minute opening diameters corresponding to the numerical aperture (NA) of the objective lens, the installation angle is precisely adjusted for each of the disk units, thereby making it possible to optimize the optical conditions, such as resolution, brightness, etc. of an image.

According to another form, the present invention provides a specimen observation method using a microscope apparatus, the method including the steps of: radiating illumination light onto a specimen; detecting observation light that returns, from the specimen irradiated with the illumination light, via the light path of the illumination light in the reverse direction; adjusting the position and the angle of the optical axis of the illumination light in a state in which a disk unit is removed from the optical axis of the illumination light, the disk unit being obtained by integrally forming a first disk in which a plurality of minute openings are arranged in an arrayed manner around a central shaft and a second disk in which a plurality of microlenses are arranged in an arrayed manner around the central shaft in the same pattern as the plurality of minute openings; adjusting, thereafter, the installation angle of the disk unit in the state in which the disk unit is inserted onto the optical axis of the illumination light; and adjusting, thereafter, the angle of the optical axis of the illumination light and the installation angle of the disk unit in the state in which the disk unit is still inserted onto the optical axis of the illumination light.

According to the above-described form, the position and the angle of the optical axis of the illumination light are adjusted with the disk unit removed from the optical axis of the illumination light, to align the optical axis of the illumination light with the optical axis of the objective lens, thereby making it possible to increase the amount of detected observation light and to reduce so-called image shift. In this state, the disk unit is inserted onto the optical axis of the illumination light, and the installation angle of the disk unit is adjusted in accordance with the inclination of the illumination light axis, thereby making it possible to increase the amount of transmitted illumination light in the disk unit, whereas the microlenses are inclined, thereby causing image shift.

Thus, from this state, the angle of the optical axis of the illumination light and the installation angle of the disk unit are further fine-adjusted, thereby making it possible to suppress image shift while ensuring as much transmitted illumination light in the disk unit and as much detected observation light as possible. Accordingly, while ensuring sufficient illumination intensity on the specimen surface, a high-definition image can be acquired by suppressing image shift.

According to still another form, the present invention provides a specimen observation method using a microscope apparatus, the method including the steps of: radiating illumination light onto a specimen; detecting observation light that returns, from the specimen irradiated with the illumination light, via the light path of the illumination light in the reverse direction; adjusting the position and the angle of the optical axis of the illumination light in the state in which a disk unit is removed from the optical axis of the illumination light, the disk unit being obtained by integrally forming a first disk in which a plurality of minute openings are arranged in an arrayed manner around a central shaft and a second disk in which a plurality of microlenses are arranged in an arrayed manner around the central shaft in the same pattern as the plurality of minute openings; adjusting, thereafter, the installation angle of the disk unit in the state in which the disk unit is inserted onto the optical axis of the illumination light; and adjusting, thereafter, the position of the objective lens in a direction intersecting the optical axis of the illumination light in the state in which the disk unit is still inserted onto the optical axis of the illumination light.

According to the above-described form, compared with a case in which the installation angle of the disk unit and the angle of the optical axis of the illumination light are adjusted, it is possible to suppress image shift while ensuring as much transmitted illumination light in the disk unit and as much detected observation light as possible, with ease and accuracy. Therefore, ensuring sufficient illumination intensity on the specimen surface and suppressing image shift are easily achieved, thus making it possible to acquire a higher definition image.

REFERENCE SIGNS LIST 1, 50 microscope apparatus
7 disk unit
11 objective lens
15 dichroic mirror (beam splitter)
19 illumination-light-axis adjustment mechanism (illumination-light-axis adjustment portion)
21 installation-angle adjustment mechanism (installation-angle adjustment portion)
23 unit insertion/removal mechanism (unit support portion)
25 pinholes (minute openings)
27 pinhole array disk (first disk)
29 microlenses
31 microlens array disk (second disk)
51 position adjustment mechanism (position adjustment portion)
S specimen

The invention claimed is:

1. A microscope apparatus comprising:
a disk unit including a first disk in which a plurality of minute openings are arranged in an arrayed manner around a central shaft and a second disk that is disposed with a gap with respect to the first disk in an axial direction of the central shaft and in which a plurality of microlenses are arranged in an arrayed manner around the central shaft in a same pattern as the plurality of minute openings;
a rotary drive portion that rotates the disk unit about the central shaft;
a beam splitter that focuses illumination light transmitted through the microlenses of the disk unit on the minute openings corresponding to the microlenses and that splits off, from a light path of the illumination light, observation light from a specimen, which has passed through the minute openings in a reverse direction from the illumination light;
an objective lens that radiates the illumination light that has passed through the minute openings onto the specimen and that collects the observation light from the specimen and guides the observation light to the minute openings;
an illumination-light-axis adjustment portion that can adjust a position and an angle of an optical axis of illumination light incident on the beam splitter;
an installation-angle adjustment portion that can adjust an installation angle of the disk unit; and
a unit support portion that supports the disk unit in a manner allowing the disk unit to be removably inserted onto the optical axis of the illumination light,
wherein the installation-angle adjustment portion can incline the central shaft of the disk unit in an X-direction and in a Y-direction intersecting the central shaft.

2. A microscope apparatus according to claim 1, further comprising a position adjustment portion that can adjust a position of the objective lens in a direction intersecting the optical axis of the illumination light.

3. A microscope apparatus according to claim 1, wherein the illumination-light-axis adjustment portion comprises:
an optical-axis adjustment memory that can store adjustment amounts for the position and the angle of the optical axis of the illumination light in a state in which the disk unit is removed from the optical axis of the illumination light and in a state in which the disk unit is inserted onto the optical axis of the illumination light; and
an optical-axis electric drive unit that adjusts the position and the angle of the optical axis of the illumination light based on the adjustment amounts stored in the optical-axis adjustment memory.

4. A microscope apparatus according to claim 1, further comprising a plurality of the disk units that have different minute opening diameters from each other,
wherein the unit support portion supports the disk units in a switchable manner allowing the disk units to be removably inserted onto the optical axis of the illumination light; and
wherein the installation-angle adjustment portion comprises:
a disk adjustment memory that can store an adjustment amount for the installation angle of the disk unit in the state in which any one of the plurality of the disk unit is inserted onto the optical axis of the illumination light; and
a disk electric drive unit that adjusts the installation angle of the disk unit based on the adjustment amount stored in the disk adjustment memory.

5. A microscope apparatus according to claim 1, further comprising:

a plurality of the disk units that have different minute opening diameters from each other; and a plurality of the installation-angle adjustment portions that can adjust the installation angles of the disk units individually, wherein the unit support portion supports the disk units in a switchable manner allowing the disk units to be removably inserted onto the optical axis of the illumination light.

6. A specimen observation method using a microscope apparatus, the method comprising:

radiating illumination light onto a specimen;

detecting observation light that returns, from the specimen irradiated with the illumination light, via a light path of the illumination light in a reverse direction;

adjusting a position and an angle of an optical axis of the illumination light in a state in which a disk unit is removed from the optical axis of the illumination light, the disk unit including a first disk in which a plurality of minute openings are arranged in an arrayed manner around a central shaft and a second disk in which a plurality of microlenses are arranged in an arrayed manner around the central shaft in a same pattern as the plurality of minute openings;

adjusting, thereafter, an installation angle of the disk unit in a state in which the disk unit is inserted onto the optical axis of the illumination light; and adjusting, thereafter, the angle of the optical axis of the illumination light and the installation angle of the disk unit in the state in which the disk unit is still inserted onto the optical axis of the illumination light.

7. A specimen observation method using a microscope apparatus, the method comprising:

radiating illumination light onto a specimen;

detecting observation light that returns, from the specimen irradiated with the illumination light, via a light path of the illumination light in a reverse direction;

adjusting a position and an angle of an optical axis of the illumination light in a state in which a disk unit is removed from the optical axis of the illumination light, the disk unit including a first disk in which a plurality of minute openings are arranged in an arrayed manner around a central shaft and a second disk in which a plurality of microlenses are arranged in an arrayed manner around the central shaft in a same pattern as the plurality of minute openings;

adjusting, thereafter, an installation angle of the disk unit in the state in which the disk unit is inserted onto the optical axis of the illumination light; and adjusting, thereafter, a position of an objective lens in a direction intersecting the optical axis of the illumination light in the state in which the disk unit is still inserted onto the optical axis of the illumination light.

* * * * *